United States Patent
Henriquez et al.

[11] Patent Number: 5,129,403
[45] Date of Patent: Jul. 14, 1992

[54] METHOD AND APPARATUS FOR DETECTING AND TRANSDUCING INTERSACCULAR ACOUSTIC SIGNALS

[75] Inventors: Theodore A. Henriquez; Allan C. Tims, both of Orlando, Fla.

[73] Assignee: The United States of America as represented by the Secretary of the Navy, Washington, D.C.

[21] Appl. No.: 617,469

[22] Filed: Nov. 13, 1990

Related U.S. Application Data

[63] Continuation of Ser. No. 181,606, Apr. 14, 1988, abandoned.

[51] Int. Cl.$^5$ .................................................. A61B 7/00
[52] U.S. Cl. ........................................ 128/773; 381/169
[58] Field of Search ...... 128/773, 715, 660.04–660.10; 381/153–154, 169, 187–188

[56] References Cited

U.S. PATENT DOCUMENTS

| | | |
|---|---|---|
| 3,545,260 | 12/1970 | Lichtenstein et al. . |
| 3,555,187 | 1/1971 | Rowley ................... 128/715 |
| 3,682,161 | 8/1972 | Alibert .................. 128/715 X |
| 3,948,248 | 4/1976 | Zuckerman et al. . |
| 4,008,711 | 2/1977 | Olinger et al. ............ 128/773 X |
| 4,258,229 | 3/1981 | Eggert et al. ............. 128/773 |
| 4,319,580 | 3/1982 | Colley et al. . |
| 4,407,293 | 10/1983 | Suarez, Jr. et al. ........ 128/660.1 X |
| 4,446,395 | 5/1984 | Hadjicostis . |
| 4,508,121 | 4/1985 | Myers . |
| 4,517,985 | 5/1985 | Teslawski et al. ........ 128/660.1 |
| 4,598,590 | 7/1986 | Busch-Vishniac et al. ..... 73/724 |
| 4,672,976 | 6/1987 | Kroll ..................... 128/773 X |
| 4,674,514 | 6/1987 | Abbott et al. ............. 128/660.09 |
| 4,699,150 | 10/1987 | Kawabuchi et al. .......... 128/660.1 |
| 4,721,113 | 1/1988 | Stewart et al. . |
| 4,777,937 | 10/1988 | Rush et al. ................ 600/27 |

OTHER PUBLICATIONS

Olinger et al., "Electronic Stethoscope for Detection of Cerebral Aneurysm", pp. 298–311.
Sekhar et al., "Origin, Growth, and Rupture of Saccular Aneurysms"; *Neurosurgery*, vol. 8, No. 2, 1981, pp. 248–260.
L. N. Sekhar et al., "Origin, Growth, and Rupture of Saccular Aneurysms: A Review", Neurosurgery 8, 248 (No. 2) (1981).

*Primary Examiner*—William E. Kamm
*Assistant Examiner*—John P. Lacyk
*Attorney, Agent, or Firm*—Thomas E. McDonnell; Edward F. Miles

[57] ABSTRACT

An apparatus and method for detecting acoustic signals originating in a brain, such as those that characterize intersaccular aneursyms. The apparatus has a piezoelectric detector mounted with a cupping receptacle, the receptacle formed to receive an acoustic matching medium and press the medium against the eye socket of a patient. In this manner, the apparatus provides an acoustic path between the brain and the detector that is inherently low loss and acoustically matched, making for a system that is inherently sensitive. In particular embodiments, the cupping structure can be goggles which can be mounted on the patient's head for convenience, or can be of a form enabling a technician to press the structure against the eye socket.

15 Claims, 3 Drawing Sheets

METHOD AND APPARATUS FOR DETECTING AND TRANSDUCING INTERSACCULAR ACOUSTIC SIGNALS

This is a continuation of copending application Ser. No. 07/181,606 filed on Apr. 14, 1988 which is now abandoned.

BACKGROUND OF THE INVENTION

The invention pertains to acoustic detectors, and in particular those used as medical diagnostic instruments.

Many anatomical processes create turbulence, and hence generate characteristic acoustic signals, an example of which is an intersaccular aneurysm which results from the wall of an intracranial artery becoming dangerously weakened. Under normal systolic pressure, such a weakened arterial wall distends exaggeratedly, generating in the surrounding fluid and soft tissue acoustic waves having a bandwidth and temporal shape characteristic of the aneurysmal condition. Because the consequences of a ruptured aneurysm can be so drastic, and because aneurysms are often asymptomatic until rupture, any device that can detect and identify these characteristic acoustic signals would be most welcome. Unfortunately, the skull, being very rigid compared to surrounding fluid and soft tissues, constitutes both a damping and reflective barrier for such signals. Consequently, any detection system that attempts to detect acoustic signals after they have traversed the skull will inherently have a poor signal to noise ratio and poor sensitivity.

SUMMARY OF THE INVENTION

Accordingly, it is an object of this invention to enable the detection of acoustic signals that originate in, and propagate through, a brain.

Another object of this invention is to do so by providing the signals with an acoustic flow path between the brain and an acoustic detector that is unimpeded by acoustically rigid media, such as bone.

Another object of this invention is to provide such a flow path that has, along its entire length, a relatively constant specific acoustic impedance of about that of intercranial tissue and fluids, i.e. of about that of water.

Another object of the invention is to enable one to transduce such signals into a form usable by electronic signal processors.

Another object of the invention is to provide an acoustic sensor of inherently high sensitivity.

Another object of the invention is to permit the detection of acoustic signals characteristic of an intersaccular aneurysm.

In accordance with these and other objects that shall become apparent hereinafter, the invention features an apparatus, and method for using the apparatus, having an acoustic sensor effective to transduce such acoustic signals into electric signals suitable for subsequent data processing, and a cupping structure for disposing an acoustic matching medium between the patient's eye socket and the sensor. Because the soft tissue of the brain and surrounding fluids all have acoustic impedances approximately that of water, as does the eyeball, eyelid, and their associated tissues, acoustic signals in the brain have an inherently low loss, constant acoustic impedance, path to the outer surface of the eyelid. The cupping structure locates against the eye socket in a manner to dispose the matching medium against the eye socket so as to form an additional acoustic flow path from the eye socket to the sensor, this also forming a continuous flowpath between the brain and the sensor. This flow path is of low and relatively constant acoustic impedance, permitting a high signal-to-noise ratio of signals traveling between the brain and the sensor. The sensor can be in the form of a piezoelectric disk that is polarized in the direction parallel to acoustic signals incident upon the detector in a manner to exploit the inherent stress strain relationships in the disk to provide a sensor of exceptional inherent sensitivity. In two particular embodiments, the cupping structure is in the form of goggles with which the acoustic detector is mounted, the goggles being mountable on a patient's head for easy use. A third embodiment dispenses with goggles, and is in the form of a hand held device that a technician can locate against a patient's eye socket manually. The resulting apparatus provides a simple, efficient, and inexpensive system which, because of the acoustically well matched and inherently low loss flow path between the origin of the acoustic signals and the sensor of the acoustic signals, is inherently of high sensitivity, this sensitivity being further increased by the inherently sensitive acoustic sensors employed. When combined with an electronic circuit to decode transduced acoustic signals (e.g., a fast fourier transform circuit), one can detect the presence of life threatening conditions such as aneurysms in time to treat them safely.

The invention is more fully understood from the following detailed description, it being understood, however, that the invention is capable of extended application and is not confined to the precise details of the embodiments disclosed. Changes and modifications may be made that do not affect the spirit of the invention, nor exceed its scope, as expressed in the appended claims. Accordingly, the invention is now discussed with reference to the accompanying drawings, wherein:

BRIEF DESCRIPTION OF THE DRAWINGS

FIG. 6 shows the embodiment from the patient's line of sight.

DETAILED DESCRIPTION OF THE INVENTION

Figure 1:
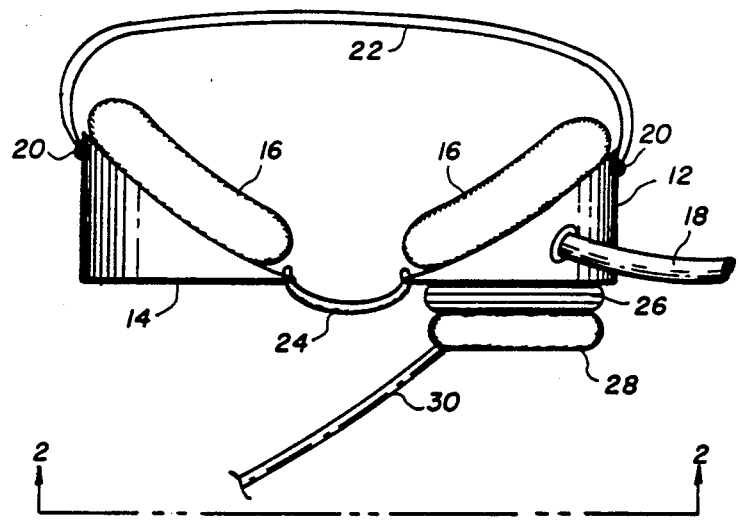
FIG. 1 is a top elevational view of one embodiment of the invention.
Figure 2:
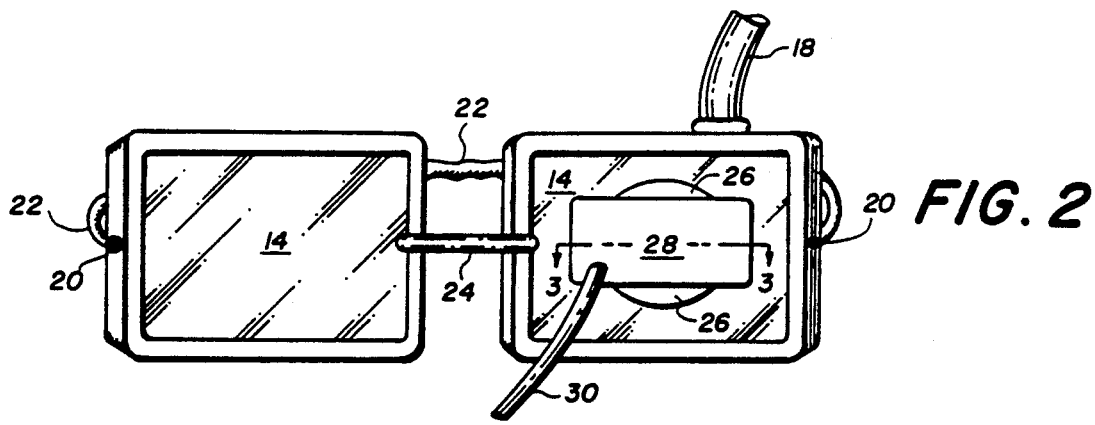
FIG. 2 is a front elevational view of the embodiment of FIG. 1, viewed in the direction of lines 2—2 of FIG. 1.

With reference to the drawing figures, and in particular FIGS. 1-2, an embodiment of the invention is illustrated in the form of a pair of goggles that can be worn on a patient's head. The goggles have goggle lenses 12, 14, preferably made of a material such as polycarbonate. Although rigid, the thickness of lens 14 is chosen to be small with respect to any acoustic wavelength of interest, rendering lens 14 effectively transparent acoustically. Located about the periphery of goggle lenses 12,14 is a sealing layer 16 (one per goggle lens) made, for example, of sponge rubber of sufficient density to hermetically seal about the periphery of lenses 12,14. Lenses 12,14 are mechanically joined together by any conventional flexible member 24, and adapted to be worn on the head of a patient by inserting headstrap 22 into mounting holes 20. Goggle lens 12 is penetrated by tube 18 in a manner that enables one to fill the inside of goggle lens 12 with a fluid. Fixidly mounted to lens 12 is a piezoelectric sensor (transducer-detector) 26, and a preamplifier stage 28, the output of which is transmitted by output wires 30.

Figure 3:
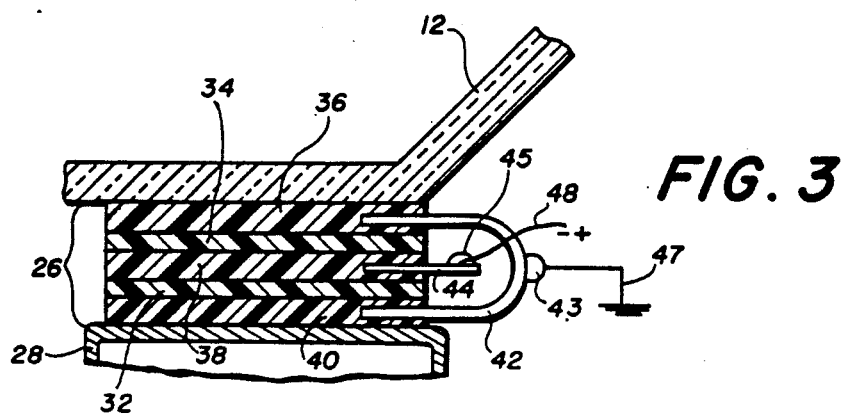
FIG. 3 is a sectional view, in the direction of lines 3—3 of FIG. 2, along the cut indicated by the dotted lines in FIG. 2.

With particular reference to FIG. 3, the details of sensor 26 are shown. Sensor 26 is in the form of a conventional two plate piezoelectric element formed of discs 32, 34 of piezoelectric material, attached to, and separated, from one another by central potting layer 38. The piezoelectric discs can be of any commercially available kind that is both sensitive and rugged, for example, polyvinalidine fluoride, and are chosen (as are all the piezoelectric elements in all embodiments described herein) in a manner known those skilled in the piezoelectric transducer art to have an acoustic bandwidth of approximately 0.1 to 2.0 khz. Discs 32, 34 are polarized in the axial direction, i.e., transverse to the circular plane in which the disks 32,34 lie. By so doing, a small stress in the annular direction produces a disproportionly large strain in the radial directions of disks 32,34, making for an unusually sensitive sensor. Potting material 38 can be of any kind known to those skilled in the acoustic art that provides electric insulation, as well as transparency to acoustic signals of interest. Examples of such potting material are: silicon rubber, polysulfide, and isocyanate based elastomers (e.g. polystyrene). Another potting layer 36 is disposed between lens 12 and piezoelectric plate 34 in a manner to adhesively and mountingly join transducer 26 to lens 12. Disposed within potting layers 36,40 are the distally opposite ends of electrode 42, which is soldered at 43 to an electrical ground connection. Similarly disposed within potting layer 38 is an electrode 44, of opposite polarity to that of electrode 42. Both electrodes 42 and 44 are joined by respective solder beads 43,45 to output wires 47,48, which together constitute the electric output of piezoelectric detector 26. The material used at 43,45 is preferably silver solder, and electrodes 42,44 are preferably gold leaf, to minimumize electrode degradation over time despite hostile environments. Electrode 42 is in the shape of a "U" so as to provide electric shielding of electrode 44 by electrode 42 in the direction transverse to piezoelectric detector 26. Experience has demonstrated that this eliminates the majority of stray signals likely to be picked up by the electrodes.

In operation, the goggle structure shown in FIGS. 1–3 is mounted on a patient's head in the conventional manner, and lenses 12 and 14 located over the patient's eyes, with sponge rubber members 16 circumferentially surrounding the eye sockets so as to provide a hermetic seal. A liquid, or otherwise readily flowable, medium for impedance matching (such as water) is injected into lens 12 via tube 18, care being taken to eliminate all air bubbles within lens 12 (which would degrade the acoustic performance of the system). Upon disposing the impedance matching medium so as to completely fill lens 12, there is created an acoustic path directly between piezoelectric sensor 26 and the interior of the patient's brain, this path constituted by the fluid and soft tissues of the brain and eye (including the patient's closed eyelid), the water or other impedance matching fluid inside lens 12, and the acoustically transparent polycarbonate or like material constituting lens 12. Any acoustic signal present within the patient's brain is provided a low loss, substantially constant acoustic impedance, path directly to sensor-transducer 26. Because the planes of piezoelectric discs 32,34 are disposed generally vertically, these planes lie generally transverse to this flow path. Thus, the direction of discs 32 and 34's polarization lie generally parallel to the flowpath, disposing sensor 26 so that acoustic signals traversing the flowpath are incident upon sensor 26 from the direction to which sensor 26 is most sensitive. Because of this path, and the inherent sensitivity of piezoelectric transducer 26, preamplifier 28 is provided with a transduced signal from sensor 26 having a good signal-to-noise ratio, and suitable for processing by whatever electronics is fed by the output cables 30 of preamplifier 28.

Figure 4:
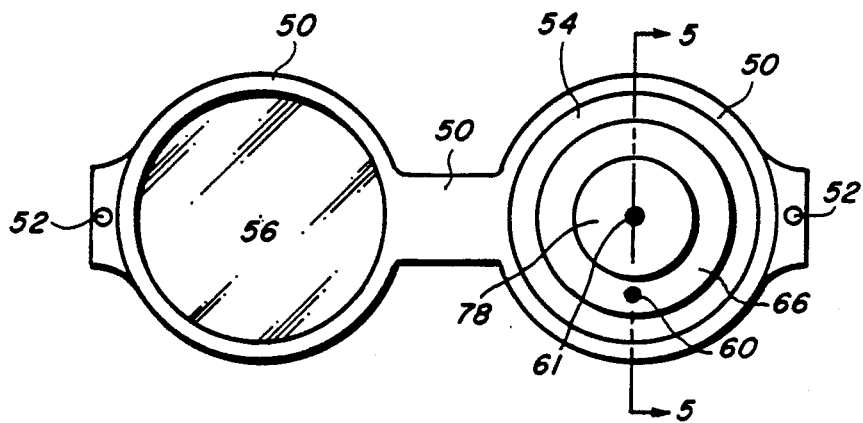
FIG. 4 is an elevational view of a second embodiment of the invention.
Figure 5:
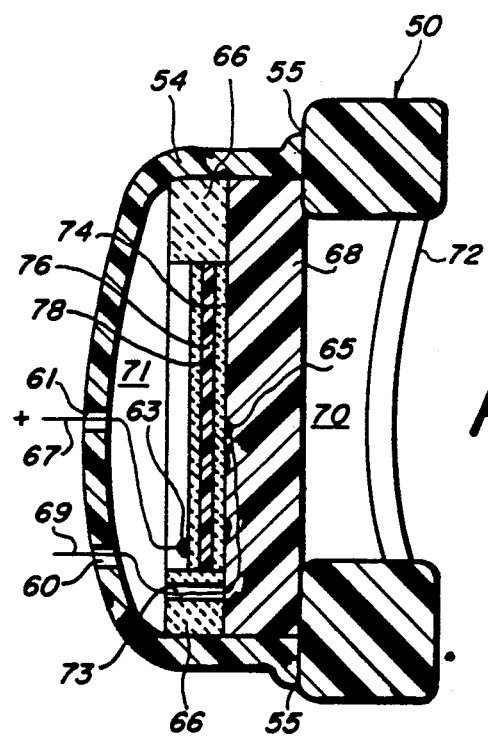
FIG. 5 is a sectional view in the direction of lines 5—5 of FIG. 4, along the cut indicated by the dotted lines of FIG. 4.

With particular reference to FIGS. 4 and 5, a second embodiment of the invention is illustrated. FIG. 4 shows, like the embodiment of FIGS. 1 through 3, a pair of goggles, which here has an outer member 50 serving as a structural framework. Extending at distally opposite ends from member 50 are flanges having holes 52 to which can be attached a head mounting strap (not shown, but typically like strap 22 of FIG. 1). Mounted annularly within structure 50 are annulus 66 and lenses 54,56, whose acoustic characteristics, for reasons made apparent hereinafter, are unimportant. Disposed annularly within the goggle associated with lens 54 is piezoelectric sensor 74,78. Sensor 74,76 can be the same piezoelectric element as used in the embodiment of FIGS. 1–3, but, because in this embodiment member 74,78 is inaccessibly mounted within goggle lens 54, member 74,78 is preferably made of lead titanate or lead zirconate, which are more rugged and hence less likely to need maintenance over time. As best seen in FIG. 5, lens 54 has openings 60,61 to accommodate electric wires exiting lens 54, lens 54 itself being attached by any appropriate and conventional means to member 50 at 55. Annulus 66 is attached to lens 54 by any conventional means, for example industrial epoxy, and is made of any hard and electrically inert structural material, such as aluminum oxide. Annulus 66 mounts the piezoelectric element which has parallel plates 74,78 of piezoelectric material separated from one another by acoustic potting material 76. Sensor 74,78 is affixed within annulus 66 by any conventional mounting means, such as the same adhesive by which annulus 66 is mounted, and is polarized in the same manner as piezoelectric discs 34,36 of FIG. -3. Between lens 54 and piezoelectric discs 74,78, is a cavity 71 which provides piezoelectric discs 74,78 air backing, allowing discs 74,78 vibrational freedom of movement responsive to incident acoustic signals. Disposed within lens 54 between structural annulus 66 and member 50 is a layer 68 of acoustical material which can be, for example, of the acoustic potting material used for member 76 and used generally in the embodiments of FIGS. 1–3. Layer 68 is flush against member 50 and annulus 66 and disk 74, so as to be in intimate acoustic contact with piezoelectric member 74. On the opposite side of layer 68 from piezoelectric disk 74 is cavity 70 which mounts over a patient's eye socket, rim 72 of member 50 being shaped to locate sealingly about the perimeter of the eye socket. Electrical wires 67,69 are soldered at 63,65 to piezoelectric disks 74,78 and exit lens 54 through holes 60,61, wire 69 traversing annulus 66 through penetration 73. The solder 63, 65, and wires 67, 69, can advantageously be the same kind used in the embodiment of FIGS. 1-3.

In operation, the goggles are placed in the conventional manner on the head of a patient, rim 72 seating about one of the patient's eye sockets. Prior to this, cavity 70, and the area within the perimeter of the eye socket, is smeared with a non-flowable acoustic matching medium, so that, upon mounting the goggles in place, the acoustic matching medium extends continuously from the patient's (typically closed) eyelid to potting layer 68. The axial depth of cavity 70 is chosen small with respect to acoustic wavelengths of interest so that the acoustic impedence across the matching medium in cavity 70 is so small as to make the matching medium virtually transparent regardless of its inherent acoustic impedence. Examples of appropriate matching media are petroleum jelly or electrocardiogram salve. Thus, in the same manner as in the embodiment of FIGS. 1-3, there extends a low loss, acoustically impedance matched, flow path from the patient's brain through the acoustic matching medium in cavity 70 and acoustic potting material 68 to the piezoelectric detector 74,78. As with the embodiment of FIGS. 1-3, detector 74,78 is polarized in its axial direction, which is also the direction generally parallel to the direction along which signals traversing the flowpath propagate. An acoustic signal originating in the patient's brain will travel along this path to sensor 74,78, at which point the acoustic signal is transduced into an electric signal manifested by a electric potential difference between wires 67 and 68, suitable for electronics processing.

Figure 6:
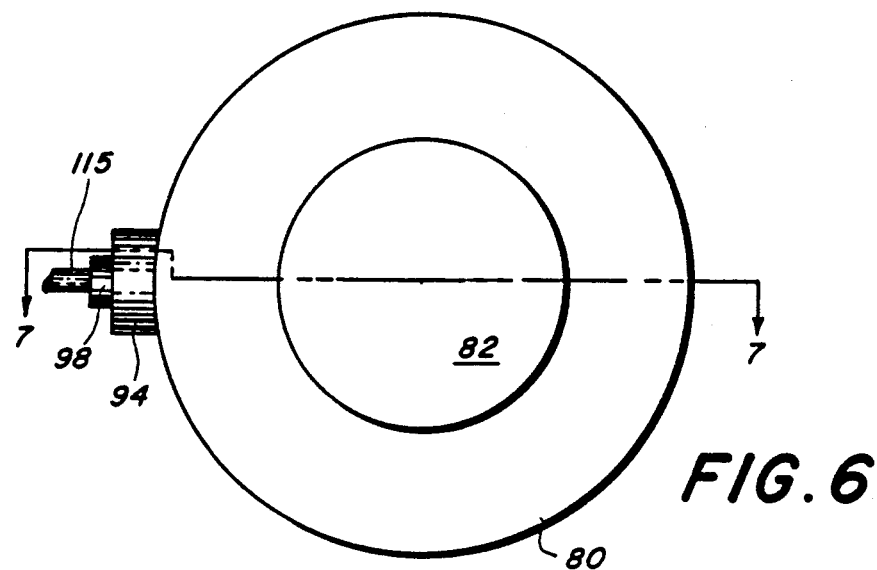
FIG. 6 is an elevational view of a third embodiment of the invention.
Figure 7:
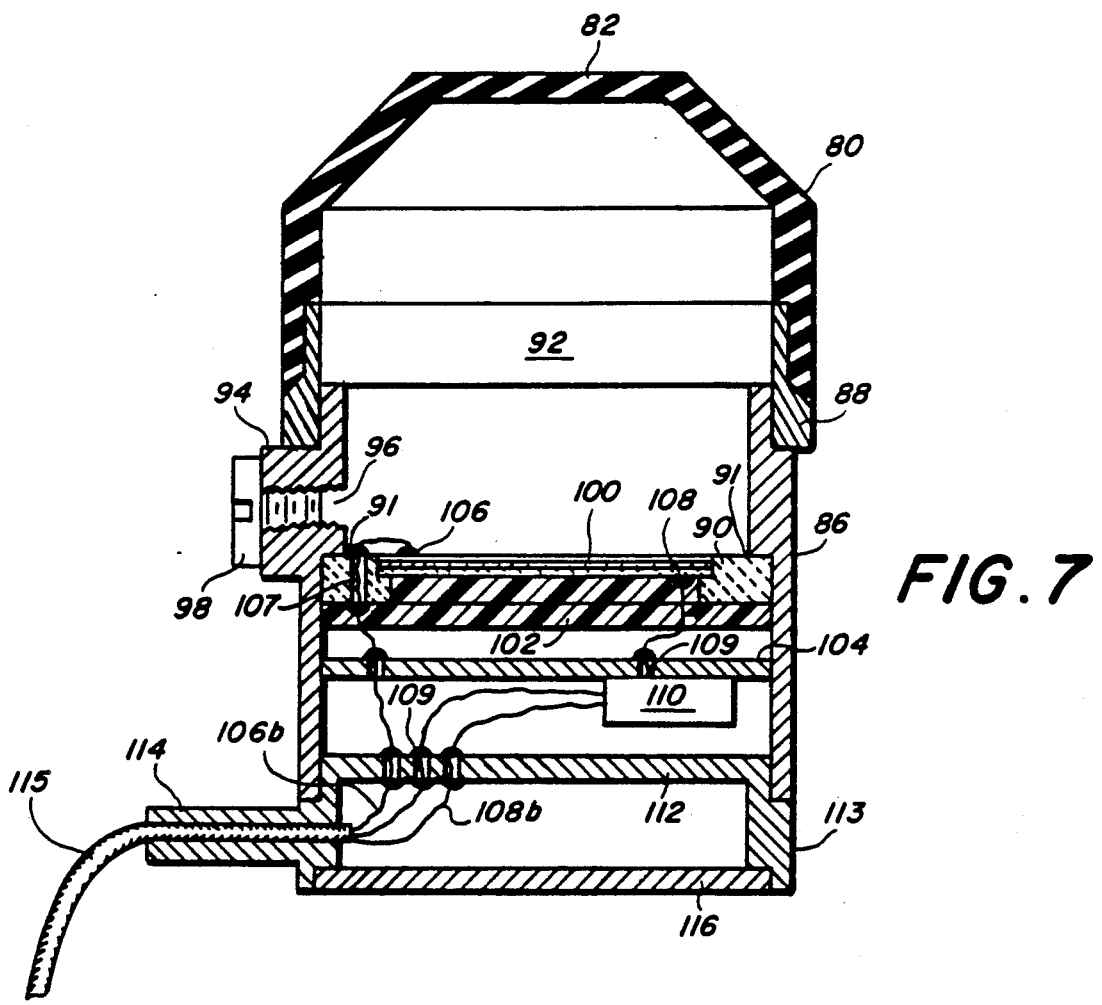
FIG. 7 is a sectional view, in the direction of lines 7—7 of FIG. 6, along the cut indicated by the dotted lines in FIG. 6.

With particular reference to FIGS. 6 and 7, a third embodiment of the invention is shown. A resilient membrane 80 is disposed over a plurality of annular walls 86, 88, to enclose a space, the top portion of which is indicated at 92. Flexible membrane 80 has a portion 82 that is thin and resilient so as to be conformable to the shape of a patient's eye. Membrane 80 can be of natural rubber, i.e. substantially pure latex, and molded or press fit over annular wall 88, which in turn is resiliently press fit over annular wall 86. Wall 86 has an annular extension 94, and a through-passage 96 communicating with space 92, which is closed off by screw 98. Walls 86,88, as well as any other structural member indicated as metallic in FIG. 7, is preferably made of stainless steel, an excellent structural material and one that is resistant to degradation, although any other material having these characteristics is acceptable. Annulus 90 is mounted within annular wall 86 against annular lip 91 and mountingly carries piezoelectric element 100, the latter preferably being the same as element 74,76,78 (FIGS. 4-5) because element 100 is permanently mounted in space 92. As with annulus 66 of FIG. 5, annulus 90 can be of aluminum oxide or any other electrically inert structural material. Annulus 90 is attached to wall 86 by an appropriate adhesive, such as an industrial epoxy (like annulus 66 of FIG. 5) and hermetically seals space 92 from the remainder of the space within walls 86,113, etc. Disposed on annulus 90 is layer 102 of acoustic potting material (of the same kind used in earlier embodiments). Layer 102 is air-backed to give piezoelectric element 100 vibrational freedom of movement in its axial direction, i.e., parallel to the direction that an acoustic signal takes in space 92 (and, ultimately, from a patient's brain). The output connection of piezoelectric element 100 corresponding to system ground is indicated at 106 which, as in earlier embodiments, is a gold leaf wire affixed to piezoelectric element 100 by silver solder. Lead 106 extends through a penetration 107 in annulus 90 through potting material 102 and penetrations in plates 104 and 112 to electric cable 115, which bundles all electric outputs for interconnection with diagnostical electronics. Similarly, the output of piezoelectric element 100 of opposite polarity from member 106 is indicated by 108, which extends through potting material 102 and a penetration in plate 104 to preamplifier 110, the output of which is fed to cable 115 via a penetration in plate 112. A third wire 109 supplies power to preamplifier 110. The wires exiting cable 115 are protected from the external elements by face plate 116, which preferably press fits into annular wall 113.

In operation, during assembly of the device shown in FIG. 6 and 7, space 92 is filled with degassed, acoustic grade, castor oil through opening 96 in annular wall 86. Upon insuring that space 92 contains no air bubbles, cap 98 is screwed into opening 96, plugging opening 96 and heremetically sealing the castor oil in space 92. A thin layer of acoustic matching material, such as petroleum jelly or electrocardiogram salve is smeared onto portion 82 of member 80, and onto the closed eyelid of the patient. A technician, grasping the device at the opposite end from portion 82, gently presses membrane portion 82 against the patient's closed eyelid. Membrane portion 82 flexibly deforms to the shape and contour of the patient's eye, insuring that the castor oil in space 92 and the patient's eyelid are separated only by a very thin film of acoustic matching material, and membrane portion 82. This done, the interior of the patient's brain and piezoelectric member 100 are connected by a low loss, acoustically well matched path, in the same manner as in the above embodiments. Stated alternatively, the fluid smeared on the patient's eye, membrane portion 82, and castor oil in space 92, together constitute the impedence matching medium of this embodiment. As in the first two embodiments, sensor 100 is axially polarized, i.e. polarized generally parallel to the flowpath's direction of propagation. The use of castor oil in cavity 92 is especially advantageous because castor oil, being a liquid, cannot support shear stress. A technician holding the device shown in FIGS. 6 and 7 to a patient's eye for any appreciable length of time will, of necessity, begin to tire, and muscle tremors from the technician must inevitably propagate into the device. Such tremors are predominately shear in nature, and, castor oil being unable to support shear stress, these tremors cannot be transmitted through cavity 92 to piezoelectric element 100. (Vibrations along walls 86,88 etc. caused by such tremors have little effect on piezoelectric member 100, most especially because member 100 is polarized transverse to the direction that these vibrations would enter member 100.)

The invention has been shown in what is considered to be the most practical and preferred embodiments. It is recognized, however, that obvious modification may occur to those with skill in the art. Accordingly, the scope of the invention is to be discerned solely by reference to the appended claims, wherein:

What is claimed and desired to be secured by Letters Patent of the United States is:

1. Apparatus for passively detecting and transducing an acoustic signal propagating through a brain in a head having an eye socket, said apparatus comprising:

sensor means for detecting said acoustic signal and transducing said acoustic signal into an electric signal;

an acoustic matching medium;

cupping means for disposing said acoustic matching medium between said sensor means and said eye socket;

wherein said cupping means is adapted to locate said acoustic matching medium effective to create an acoustic path between said brain and said sensor means, said path having an acoustic impedance along the entire length of said path of about that of water.

2. The apparatus of claim 1, wherein said apparatus is adapted to freestandingly mount said cupping means on said eye socket effective to create said acoustic path.

3. The apparatus of claim 2, wherein:

said cupping means is in the form of at least one goggle;

said sensor means comprises a piezoelectric detector, and potting means for mounting said sensor means on said goggle;

said potting means being located effective to freestandingly mount said sensor means on the surface of said at least one goggle opposite from said eye socket.

4. The apparatus of claim 2, wherein said sensor means comprises:

a piezoelectric detector;

an annulus having recess means for mountingly receiving said detector in said recess means;

rim means for sealingly locating about said eye socket;

a lens mounted on said rim means;

potting disposed in said cupping means between said rim means and said annulus effective to mount said detector within said cupping means.

5. An acoustic detector comprising:

cupping means for receiving an acoustic matching medium, said cupping means having a perimeter;

mounting means for pressing said perimeter against a surface;

sensor means for sensing and transducing acoustic signals into corresponding electric signals;

wherein said cupping means is adapted to form an acoustic path between said surface and said sensor means, said path having a specific acoustic impedance of about that of water, when said mounting means presses said perimeter against said surface effective to locate said acoustic matching medium between said sensor means and said surface.

6. A method for passively receiving acoustic signals propagating through a brain in a head having an eye socket, said method using apparatus comprising:

a means for sensing said signal, said means for sensing being adapted to transduce said acoustic signal into an electric signal;

an acoustic matching medium;

cupping means for disposing said acoustic matching medium between said means for sensing and said eye socket of said head;

wherein said method comprises steps for:

locating said acoustic matching medium in said cupping means;

placing said cupping means against said eye socket effective to dispose said acoustic matching medium between said eye socket and said means for sensing;

wherein said steps for locating and disposing are done effective to create an acoustic path between said brain and said means for sensing having an acoustic impedance along the entire length of said path of about that of water;

7. The method of claim 6, wherein said apparatus comprises means for mounting said apparatus on said head, and said method comprises a step for using said means for mounting to dispose said apparatus on said head effective to create said acoustic path between said brain and said means for sensing having said acoustic impedance along said entire length of about that of water.

8. Apparatus for sensing acoustic signals exiting through an eye or eyelid, said apparatus comprising:

an acoustic sensor;

a fluid acoustic matching medium having an acoustic impedance of about that of water;

cupping means for locating said matching medium between, and in abutting contact with, said sensor and said eye or eyelid, said locating being effective to create an acoustic path between said sensor and said eye having an acoustic impedance of about that of water.

9. The apparatus to claim 8, wherein said cupping means is at least one goggle, said at least one goggle is adapted to be freestandingly mounted about said eye effective to cause said locating of said matching medium between and in abutting contact with said sensor and said eye or eyelid.

10. The apparatus of claim 9, wherein said at least one goggle comprises tube means for filing said goggles with said matching medium effective to cause said locating of said medium between and in abutting contact with said sensor and said eye or eyelid.

11. The apparatus of claim 8, wherein said apparatus is adapted to freestandingly mount said cupping means on said eye or eyelid effective to create said acoustic path.

12. The apparatus of claim 11, wherein:

said cupping means is in the form of at least one goggle;

said sensor comprises a piezoelectric detector, and potting for mounting said sensor on said goggle;

said potting being located effective to freestandingly mount said sensor means on the surface of said cupping means opposite from said eye or eyelid.

13. The apparatus of claim 11, wherein said sensor means comprises:

a piezoelectric detector;

an annulus having recess means for mountingly receiving said detector in said recess means;

rim means for sealingly locating about said eye or eyelid;

a lens mounted on said rim means;

potting disposed in said cupping means between said rim means and said annulus effective to mount said detector within said cupping means.

14. Apparatus for sensing acoustic signals exiting through an eye or eyelid, said apparatus comprising:

an acoustic sensor;

an acoustic matching medium;

cupping means for receiving said acoustic matching medium, said cupping means comprising a rim adapted to locate about said eye or eyelid;

a resilient membrane, said membrane being disposed over said rim and adapted to locate said acoustic matching medium between and in abutting contact with said membrane and said sensor, said membrane being of a thickness selected to create, responsive to pressing said membrane against said eye eyelid, an acoustic path between said eye or eyelid and said sensor of about that of water.

15. The apparatus of claim 14, wherein:
said sensor is a piezoelectric transducer;
said apparatus further comprises a lip for receiving said transducer in a manner to mount said transducer in contact with said acoustic matching medium.

* * * * *